(12) United States Patent
Chen et al.

(10) Patent No.: US 11,395,680 B2
(45) Date of Patent: Jul. 26, 2022

(54) LOWER LIMB TRACTION DEVICE FOR INTRAMEDULLARY NAIL IMPLANTATION OPERATION

(71) Applicants: The Third Hospital of Hebei Medical University, Shijiazhuang (CN); Yingze Zhang, Shijiazhuang (CN); Wei Chen, Shijiazhuang (CN)

(72) Inventors: Wei Chen, Shijiazhuang (CN); Yingze Zhang, Shijiazhuang (CN); Zhiyong Hou, Shijiazhuang (CN); Yanbin Zhu, Shijiazhuang (CN); Juan Wang, Shijiazhuang (CN); Di Zhang, Shijiazhuang (CN); Shiji Qin, Shijiazhuang (CN)

(73) Assignees: The Third Hospital of Hebei Medical University, Hebei (CN); Yingze Zhang, Hebei (CN); Wei Chen, Hebei (CN)

( * ) Notice: Subject to any disclaimer, the term of this patent is extended or adjusted under 35 U.S.C. 154(b) by 208 days.

(21) Appl. No.: 16/819,264

(22) Filed: Mar. 16, 2020

(65) Prior Publication Data
US 2021/0059719 A1 Mar. 4, 2021

(30) Foreign Application Priority Data

Sep. 4, 2019 (CN) .......................... 201910832613.4
Oct. 9, 2019 (CN) .......................... 201910954431.4

(51) Int. Cl.
*A61B 17/66* (2006.01)
*A61B 17/72* (2006.01)
(Continued)

(52) U.S. Cl.
CPC ............ *A61B 17/66* (2013.01); *A61B 17/645* (2013.01); *A61B 17/6441* (2013.01);
(Continued)

(58) Field of Classification Search
CPC ... A61B 17/66; A61B 17/6441; A61B 17/645; A61B 17/7233; A61B 17/8872; A61B 17/90
(Continued)

(56) References Cited

U.S. PATENT DOCUMENTS

| 491,271 | A | * | 2/1893 | Rowley | ................. | A61F 5/0111 |
| | | | | | | 602/23 |
| 2,204,266 | A | * | 6/1940 | Wilcox | .............. | A61B 17/6408 |
| | | | | | | 602/39 |

(Continued)

FOREIGN PATENT DOCUMENTS

CN 106880465 B * 8/2018 ............. A61B 17/64

OTHER PUBLICATIONS

Zhao, Orthopedic Surgery Traction Diaplasis Device, 2017, Derwent 2017-47201S, 1-3 (Year: 2017).*

*Primary Examiner* — Eduardo C Robert
*Assistant Examiner* — David C Comstock
(74) *Attorney, Agent, or Firm* — Qinghong Xu

(57) ABSTRACT

A lower limb traction device for intramedullary nail implantation operation includes a chassis with a first end portion and a second end portion opposite to each other; a first slide block slidably provided at a second end portion of the chassis in a longitudinal direction of the chassis; a lower leg support plate having two opposite end portions and two opposite side portions, wherein one end portion is connected to the first slide block; an upper leg back plate having opposite end portions and opposite side portions, wherein one end portion of the upper leg back plate is connected to the second end portion of the chassis, and the other end portion of the upper leg back plate is connected to the other end of the lower leg support plate; and a pulling mechanism provided at the first end portion of the chassis.

18 Claims, 8 Drawing Sheets

(51) Int. Cl.
*A61B 17/64* (2006.01)
*A61B 17/88* (2006.01)
*A61B 17/90* (2006.01)

(52) U.S. Cl.
CPC ...... *A61B 17/7233* (2013.01); *A61B 17/8872* (2013.01); *A61B 17/90* (2021.08)

(58) Field of Classification Search
USPC ........................................ 606/54, 57, 58, 59
See application file for complete search history.

(56) References Cited

U.S. PATENT DOCUMENTS

| | | | | |
|---|---|---|---|---|
| 5,025,802 | A * | 6/1991 | Laico | A61G 13/12 128/875 |
| 5,063,918 | A * | 11/1991 | Guhl | A61F 5/04 602/40 |
| 5,669,908 | A * | 9/1997 | Gracilla | A61F 5/04 602/23 |
| 7,947,862 | B2 * | 5/2011 | Livorsi | A61B 17/1764 602/42 |
| 9,056,042 | B2 * | 6/2015 | Russell | A61G 13/1245 |
| 9,314,272 | B1 * | 4/2016 | DeMayo | A61G 13/0036 |
| 2004/0015114 | A1 * | 1/2004 | Hay | A61F 5/04 602/32 |
| 2013/0072822 | A1 * | 3/2013 | Auchinleck | A61B 90/06 600/595 |
| 2018/0221230 | A1 * | 8/2018 | Smith | A61G 13/125 |

\* cited by examiner

LOWER LIMB TRACTION DEVICE FOR INTRAMEDULLARY NAIL IMPLANTATION OPERATION

CROSS REFERENCE

This application is based upon and claims priority to Chinese Patent Application No. 201910832613.4, filed on Sep. 4, 2019; and No. 201910954431.4, filed on Oct. 9, 2019, the entire contents thereof are incorporated herein by reference.

TECHNICAL FIELD

The present disclosure relates to a lower limb traction device suitable for femur and tibia intramedullary nail implantation operation, belonging to a technical field of orthopedic medical devices.

BACKGROUND

Femur and tibia fractures are common clinical fractures. Because of strong leg muscles, the patient's tibia often suffers from shortening deformation due to pulling of the muscles after fracture, and it is difficult to make a restoration in operation and to restore the length and effectively maintain the length. If anatomical restoration cannot be performed during operation, complications such as malformation healing and poor force lines of the lower limbs may occur after operation, and thereby leading to traumatic arthritis or osteoarthritis, which seriously affects the patient's limb function and life quality.

Intramedullary nail fixing is a common treatment for the femur and tibia fractures. Traction in operation is an important method to restore the femur and tibia fractures and restore the length of the lower limbs. At present, it is common to need two assistants to assist the patient who needs traction as implanting intramedullary nail operation. The two assistants respectively hold proximal and distal ends of the broken bone to restore the femur or the tibia. However, this method often cannot stably maintain the fracture restoration and the length of the lower limb. The restoration effect is not satisfied, and thereby affecting the treatment effect; and the two assistants can occupy space of a surgeon and affect the surgeon's surgical operation.

A traction device is used to restore the fractured femur or tibia to overcome the above disadvantages, but the existing traction devices generally need to occupy the upper space of the lower limb of the patient, which affects surgical operation, and the existing traction devices all straighten the lower limb, but the intramedullary nail is implanted from the distal end of the femur or the proximal end of the tibia, so that the patient must maintain a posture of bending leg to perform the operation. Thus, it is absolutely necessary to design a lower limb traction device suitable for intramedullary nail implantation operation.

SUMMARY

According to one aspect of the present disclosure, a lower limb traction device for intramedullary nail implantation operation, including:

a chassis with a first end portion and a second end portion opposite to each other:

a first slide block slidably provided at a second end portion of the chassis in a longitudinal direction of the chassis;

a lower leg support plate having two opposite end portions and two opposite side portions, wherein one end portion is connected to the first slide block:

an upper leg back plate having opposite end portions and opposite side portions, wherein one end portion is connected to the second end portion of the chassis, and the other end portion of the upper leg back plate is connected to the other end of the lower leg support plate; and a pulling mechanism provided at the first end portion of the chassis.

According to one implementation of the present disclosure, the lower limb traction device further includes:

a first guide rail provided at a first end portion of the chassis and extending away from the chassis;

wherein the first slide block is provided on the first guide rail.

According to one implementation of the present disclosure, the lower limb traction device for intramedullary nail implantation operation further includes:

a second guide rail, fixed to an end portion of the first guide rail away from the chassis, and being perpendicular to the first guide rail; and a lifting block slidably mounted on the second guide rail:

wherein the pulling mechanism is provided on the lifting block.

According to one implementation of the present disclosure, the pulling mechanism includes:

a first nut mounted on the lifting block;

a first screw rod working in cooperation with the first nut and having an inner end portion facing to the chassis and an outer end portion distanced from the chassis;

a hand wheel mounted on the outer end portion of the first screw rod; and a traction bow mounted on the inner end portion of the first screw rod, wherein the opening end of the traction bow is provided with a connecting structure capable of mounting a traction needle.

According to one implementation of the present disclosure, the lower limb traction device further includes:

a tibia broken bone restoration mechanism, including:

at least one jacking assembly provided at a longitudinal central line position of the lower leg support plate; and at least two side pressing assemblies respectively provided on both sides of the lower leg support plate.

According to one implementation of the present disclosure, the tibia broken bone restoration mechanism further includes:

a blinding band able to surround the lower leg support plate.

According to one implementation of the present disclosure, a plurality of side mounting holes are provided on both sides of the lower leg support plate in a longitudinal direction, and the side pressing assemblies are selectively mounted in the side mounting holes.

According to one implementation of the present disclosure, the side mounting holes are threaded holes, and the side pressing assembly includes:

a side pressing plate, with a bottom end portion mounted in the side mounting holes by a fixing bolt, and an upper portion of the side pressing plate provided with a plurality of threaded holes; and a side pressing bolt selectively fitted to one of the plurality of threaded holes of the side pressing plate and extending to a direction of the lower leg support plate.

According to one implementation of the present disclosure, a plurality of middle mounting holes are provided at a longitudinal central line position of the lower leg support plate, and the jacking assembly is selectively mounted in the middle mounting hole.

According to one implementation of the present disclosure, the middle mounting holes are threaded holes, and the jacking assembly includes:

a jacking bolt selectively fitted to one of the plurality of the threaded holes.

According to one implementation of the present disclosure, the lower limb traction device further includes:

a sleeve having a lower end portion connected to the second end of the chassis, and an upper end portion with an opening;

wherein one end of the upper leg back plate is slidably received in the sleeve with respect to the sleeve.

According to one implementation of the present disclosure, the lower limb traction device further includes:

an adjusting mechanism for adjusting height of the upper leg back plate, including:

a second nut fixed on the sleeve;

a second screw rod working in cooperation with the second nut, and having one end connected to the upper leg back plate and the other end equipped with a rotating handle.

According to one implementation of the present disclosure, the lower limb traction device further includes:

a femur broken bone restoration mechanism, including:

at least one jacking assembly provided at a longitudinal central line position of the upper leg back plate; and at least two side pressing assemblies respectively provided on both sides of the upper leg back plate.

According to one implementation of the present disclosure, the lower limb traction device further includes:

two third guide rails mounted on both sides of the upper leg back plate;

two sliding frames slidably mounted on the two third guide rails, respectively; and two correcting arms, having end portions respectively connected to the top end portions of the two sliding frames, the correcting arms being provided with a connecting structure for mounting Kirschner wires, and positions of the two correcting arms being higher than the lower leg support plate.

According to one implementation of the present disclosure, the correcting arm is rotatably connected to the sliding frame, and the lower limb traction device further includes:

a fixing arm, having one end fixed on the upper portion of the sliding frame and positioned under the correcting arm, and the fixing arm being provided with a threaded hole; and an angle adjusting bolt fitted to the threaded hole, one end of the angle adjusting bolt abuts against the other end of the correcting arm to adjust an angle of the correcting arm.

According to one implementation of the present disclosure, the lower limb traction device further includes:

a sliding frame limiting device, including:

a fixing block, fixed to the third guide rail and provided with a threaded hole; and a limiting bolt matched with the threaded hole on the fixing block and provided in parallel with the third guide rail, and the end portion of the limiting bolt abuts against the bottom end portion of the sliding frame.

According to one implementation of the present disclosure, the lower limb traction device further includes two Kirschner wires provided between the connecting structures of the two correcting arms.

According to one implementation of the present disclosure, an upper surface of the lower leg support plate or the upper leg back plate has an arc-shaped concave surface.

According to one implementation of the present disclosure, adjustable legs are provided on the bottom portion of the chassis.

According to one implementation of the present disclosure, the lower limb traction device further includes a traction needle provided at the connecting structure of an opening end of the traction bow.

According to the other aspect of the present disclosure, a lower limb traction device for intramedullary nail implantation operation includes a chassis, a lower leg support plate, an upper leg back plate, a first slide block, a traction needle, a traction bow, and a pulling mechanism. The first slide block is mounted on the axial sliding channel on the chassis and is provided with a slide block locking screw. The lower leg support plate and the upper leg back plate are hinged in the shape of angle. The lower end of the upper leg back plate is rotatably connected to a head end of the chassis. The lower end of the leg support plate is rotatably connected to the first slide block. The patient's upper leg and the lower leg rest on the upper leg back plate and the lower leg support plate, respectively. The traction needle penetrates through the distal end of the ankle bone or the tibia of the patient. The bow back of the traction bow is connected to a tail end of the chassis by a pulling mechanism.

In the lower limb traction device for intramedullary nail implantation operation, the pulling mechanism includes a second guide rail, a lifting block, a first nut, a first screw rod, and a hand wheel. The second guide rail is fixed at the tail end of the chassis. The lifting block is slidably connected to the second guide rail and is provided with a lifting block locking screw. The first nut is rotationally connected to the lifting block. The first screw rod is matched with the first nut through a thread. The first screw rod has one end rotatably connected with the bow back of the traction bow and the other end fixedly connected with the hand wheel.

In the lower limb traction device for intramedullary nail implantation operation, the lower end of the upper leg back plate is rotationally connected to the head end of the chassis through a sleeve. The sleeve is sleeved on the lower end of the upper leg back plate and is slidably connected to the upper leg back plate. The lower end of the sleeve is rotatably connected to the head end of the chassis through a horizontal axis perpendicular to the chassis. An adjusting mechanism is connected between the upper leg back plate and the sleeve. The adjusting mechanism includes a screw rod and a second nut. The second nut is fixed on the sleeve, the screw rod is matched with the second nut through the thread. The screw rod has one end rotatably connected with an upper leg back plate and the other end provided with a rotating handle.

The lower limb traction device for intramedullary nail implantation operation, in the construction, further includes a tibia broken bone restoration mechanism. The tibia broken bone restoration mechanism includes a blinding band, a jacking bolt, a side pressing plate, a side pressing bolt, and a fixing bolt. The patient's lower limb is bond to the lower leg support plate or the upper leg back plate by the binding band. The jacking bolt is screwed into a jacking threaded holes of the lower leg support plate or the upper leg back plate and is pressed against the lower portion of the patient's lower limb, and the lower end of the side pressing plate is fixed on the side portion of the lower leg support plate or the upper leg back plate by the fixing bolt, and the side pressing bolt is screwed into the threaded hole on the side pressing plate and presses against the side portion of the lower limb of the patient.

In the lower limb traction device for intramedullary nail implantation operation, a multiple fixed threaded holes are provided on both sides of the lower leg support plate and upper leg back plate, and a plurality of jacking threaded holes are provided in the middle portion of the lower leg support plate and the upper leg back plate. The fixed threaded holes and the jacking threaded holes are evenly arranged along a length direction of the lower leg support plate and the upper leg back plate.

In the lower limb traction device for intramedullary nail implantation operation, a notch is provided in the middle portion of the tail end of the chassis. The two second guide rails are respectively fixed on both sides of the notch. The lifting block is slidably connected with the two second guide rails. The first nut and the first screw rod correspond to the notch at the tail end of the chassis.

In the lower limb traction device for intramedullary nail implantation operation, the lower portion of the chassis is provided with an adjustable leg.

In the lower limb traction device for intramedullary nail implantation operation, the side of the lower leg support plate and the upper leg back plate corresponding to the lower leg and the upper leg of the patient is an arc-shaped concave surface.

According to another aspect of the present disclosure, a lower limb skeletal restoration device for intramedullary nail implantation operation, in the construction, includes a chassis, a first slide block, a lower leg support plate, an upper leg back plate, and two Kirschner wires and two adjustable brackets. The first slide block is mounted on the axial sliding channel on the chassis and is provided with a sliding block locking screw. The lower leg support plate and the upper leg back plate are hinged in the shape of angle. The lower leg support plate is hinged with the first slide block, and the lower end of the upper leg back plate is rotatably connected to the head end of the chassis by an adjusting mechanism. Two adjustable brackets are symmetrically mounted on both sides of the upper leg back plate. The upper led and the lower leg respectively rest on the upper leg back plate and the lower leg support plate. The two Kirschner wires penetrate through the distal end of the femur of the patient, and two ends of each Kirschner wire are respectively placed on two adjustable brackets.

In the lower limb skeletal restoration device for intramedullary nail implantation operation, the adjustable bracket includes a third guide rail, a sliding frame, a fixing block, a correcting arm, a limiting bolt, and an angle adjusting bolt. The third guide rail is fixed on the side of the upper leg back plate. The sliding frame is slidably connected to the third guide rail. The fixing block is fixed at the lower end of the third guide rail. The limiting bolt is screwed into the threaded hole on the fixing block and abuts against the lower end of the sliding frame. The correcting arm supports the end portions of the two Kirschner wires. The head end of the correcting arm is hinged with the upper end of the sliding frame. The angle adjusting bolt is screwed into the threaded hole on the sliding frame and abuts against the lower portion of the tail end of the correcting arm.

The present disclosure can keep the patient in a bending leg state and reliably pull the tibia, and all parts are not higher than the lower limb of the patient, which does not affect the operation. The device can make sure the femur and tibia intramedullary nail implantation operation successful, and improve the quality and efficiency of the operation. In addition, the present disclosure has advantages of simple structure, low cost, and reliable performance.

BRIEF DESCRIPTION OF THE DRAWINGS

The present disclosure will be described in further detail below with reference to the accompanying drawings and the specific embodiments.

DETAILED DESCRIPTION

Now, the exemplary implementations will be described more completely with reference to the accompanying drawings. However, the exemplary implementations can be done in various forms and should not be construed as limiting the implementations as set forth herein. Instead, these implementations are provided so that this disclosure will be thorough and complete, and concept of the exemplary implementation will be fully conveyed to those skilled in the art. Same reference numbers denote the same or similar structures in the figures, and thus the detailed description thereof will be omitted.

The relative words, such as "upper" or "lower", as used herein, are directed to describe a relative relationship between one component and the other component of an icon. These words are used herein for convenience only, for example, according to the direction of the illustrative examples as shown in the figures. It should be appreciated that if the referenced device is inversed upside down, the component indicated as being the "upper" side would become the component on the "lower" side. When one structure is "on" another structure, it is possible to indicate that the one structure is integrally formed on the other structure, or the one structure is "directly" arranged on the other structure, or one structure is "indirectly" formed on the other structure by means of a further structure.

The terms "a", "an", "the", "said" and "at least one", when describing element/constituent/or the like as described and/or shown herein, are used to express the presence of one or more the element/constitute/or the like. The terms "include", "comprise" and "have", as used herein, are intended to be inclusive, and mean there may be additional elements/constituents/or the like other than the listed elements/constituents/or the like.

Figure 1:
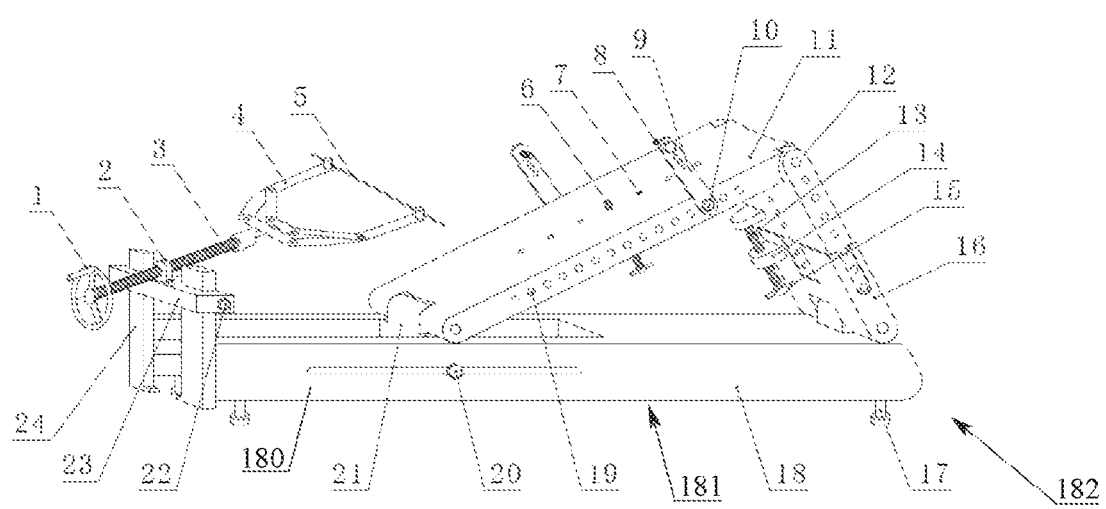
FIG. 1 is a perspective structural schematic view of one embodiment of a lower limb traction device for intramedullary nail implantation operation of the present disclosure.
Figure 2:
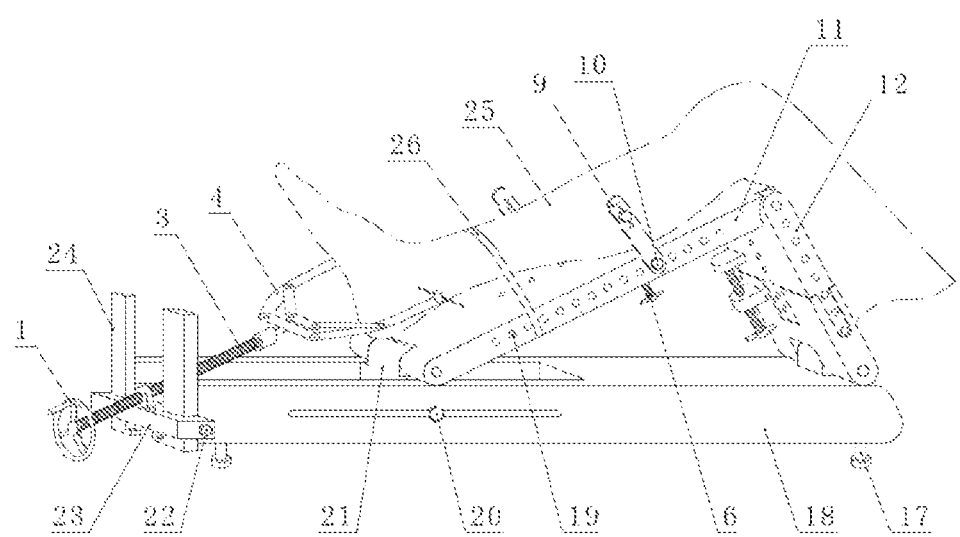
FIG. 2 is a use state schematic view of the intramedullary nail implantation operation for a tibia of the present disclosure.

Referring to FIGS. 1 and 2, one embodiment of a lower limb traction device for intramedullary nail implantation operation of the present disclosure includes: a chassis 18, which has a first end portion 181 and a second end portion 12, and which may be a rectangular frame structure or other structures; a first slide block 21, which is slidably disposed at the second end portion 182 of the chassis 18 along a longitudinal direction of the chassis 18; a lower leg support plate 11, which has opposite end portions and opposite side portions, wherein one end portion is connected to the first slide block 21, and which is used for supporting a patient's lower leg; a upper leg back plate 12, which has opposite end portions and opposite side portions, wherein one end is connected to the second end portion 182 of the chassis 18, the other end of the upper leg back plate 12 is connected to the other end of the lower leg support plate 11, and which is used for supporting the patient's upper leg; and a pulling mechanism, which is disposed at the first end portion 181 of the chassis 18.

According to one embodiment of the present disclosure, the lower limb traction device further includes a first guide rail 180 disposed at the first end portion 181 of the chassis 18 and extending away from the chassis 18, wherein the first slide block 21 is disposed on the first guide rail 180.

According to one embodiment of the present disclosure, the lower limb traction device further includes: a second guide rail 24, which is fixed to the end portion of the first guide rail 180 far away from the chassis 18 and perpendicular to the first guide rail 180, wherein the first guide rail 180 is, for example, a horizontal guide rail, and the second guide rail 24 is, for example, a vertical guide rail; and a lifting block 23, which is slidably mounted on the second guide rail 24; wherein the pulling mechanism is disposed on the lifting block 23.

According to one embodiment of the present disclosure, the pulling mechanism includes: a first nut 2, which is mounted on the lifting block 23; a first screw rod 3, which cooperates with the first nut 2 and has an inner end portion facing to the chassis 18 and an outer end portion distanced from the chassis 18; a hand wheel 1, which is mounted at the outer end portion of the first screw rod 3; and a traction bow 4, which is mounted at the inner end portion of the first screw rod 3, wherein an opening end of the traction bow 4 is provided with a connecting structure capable of mounting a traction needle 5. The connecting structure can be two convex blocks relatively fixed to the opening end of the traction bow 4, and the two convex blocks are provided with two opposite holes, through which the two ends of the traction needle 5 can pass to be mounted on the traction bow 4.

According to one embodiment of the present disclosure, the lower limb traction device further includes a tibial fracture restoration mechanism. The tibial fracture restoration mechanism includes: at least one jacking assembly arranged at a longitudinal central line position of the lower leg support plate 11; and at least two lateral pressing assemblies respectively arranged at two sides of the lower leg support plate 11.

Further, the tibial fracture restoration mechanism further includes a binding band 26 that can surround the lower leg support plate 11.

According to one embodiment of the present disclosure, a plurality of side mounting holes 19 are provided on both sides of the lower leg support plate 11 in a longitudinal direction thereof, and the side pressing assemblies are selectively mounted to the side mounting holes 19.

According to one embodiment of the present disclosure, wherein the side mounting holes 19 are threaded holes. The side pressing assembly includes: a side pressing plate 9, the bottom end portion of which is mounted to the side mounting hole 19 through a fixing bolt 10, and the upper portion of which is provided with a plurality of threaded holes; and a side pressing bolt 8, which is selectively fitted to one of the plurality of threaded holes of the side pressing plate 9 and extends in the direction of the lower leg support plate 11.

According to one embodiment of the present disclosure, a plurality of middle mounting holes 7 are provided at the longitudinal center line position of the lower leg support plate 11, and the jacking assembly is selectively mounted in the middle mounting holes 7.

According to one embodiment of the present disclosure, wherein the middle mounting holes 7 are threaded holes. The jacking assembly includes a jacking bolt 6 that is selectively fitted to one of the plurality of threaded holes.

According to one embodiment of the present disclosure, the lower limb traction device further includes a sleeve 16, which has a lower end portion connected to the second end portion of the chassis 18 and an upper end portion having an opening; wherein one end portion of the upper leg back plate 12 is slidably received in the sleeve 16 relative to the sleeve 16.

According to one embodiment of the present disclosure, the lower limb traction device further includes an adjusting mechanism for adjusting height of the upper leg back plate 12. The adjusting mechanism includes: a second nut 14 fixed on the sleeve 16; and a second screw rod 13 cooperating with the second nut 14, wherein the second screw rod 13 has one end connected to the upper leg back plate 12, and the other end provided with a rotating handle 15.

According to one embodiment of the present disclosure, the lower limb traction device further includes a femoral fracture restoration mechanism. The femoral fracture restoration mechanism includes: at least one jacking assembly arranged at the longitudinal central line position of the upper leg backup plate 12; and at least two side pressing assemblies respectively arranged on both sides of the upper leg back plate 12.

According to one embodiment of the present disclosure, an upper surface of the lower leg support plate 11 or the upper leg back plate 12 has an arc-shaped concave surface, which can conform to lower profiles of the lower leg and the upper leg of the patient to make supporting more stable and comfortable.

According to one embodiment of the present disclosure, an adjusting leg is provided on the bottom of the chassis 18, for adjusting the height of the chassis 18.

According to one embodiment of the present disclosure, the lower limb traction device further includes a traction needle 5 of the connecting structure arranged at the opening end of the traction bow 4, and the connecting structure may be holes arranged opposite to each other.

Referring to FIGS. 1 and 2, the lower leg support plate 11, the upper leg back plate 12 and the chassis 18 form a stable triangular support body, for supporting the patient's lower limb 25 and mounting various traction components. The second guide rail 24, the first slide block 21, the hand wheel 1, the first nut 2, the first screw rod 3, the traction bow 4 and the traction needle 5 are used for pulling a distal end of the tibia of the patient. The second screw rod 13, the second nut 14, the rotating handle 15 and the sleeve 16 are used to adjust a height of upper leg back plate 12, so that traction on the distal end of femur can be realized. The jacking bolt 6, the side pressing bolt 8, the side pressing plate 9, the fixing bolt 10 and the binding band 26 are used for adjusting a posture of a pulled broken bone and restoring the broken bone.

The chassis 18 is placed on an operating bed, and the height of the chassis can be adjusted by four adjustable legs 17 at the lower part of the chassis to adapt to different patients. The patient's lower leg and upper leg respectively rest on the lower leg support plate 11 and the upper leg back plate 12 to form a bending leg state, in order to facilitate for implantation of the intramedullary nail from a proximal end of the tibia or a distal end of the femur. The side of the lower leg support plate 11 and the upper leg back plate 12 corresponding to the patient's lower limb 25 form an arc concave surface, to improve stability of the lower limb and ensure quality of the operation. The lower leg support plate 11, the upper leg back plate 12 and the chassis 18 form a triangular structure, and the height and an inclination angle of the upper leg back plate 12 are adjustable, so that the operation is more flexible and convenient. A tail end of the chassis 18 is provided with a notch, to increase a moving range of the first screw rod 3 and facilitate for adjusting the pulling direction.

As performing the tibial intramedullary nail implantation operation, it is required that the traction needle 5 is used, the traction bow 4 pulls the patient's tibia, the traction needle 5 can penetrate through the patient's ankle bone and also penetrate through the distal end of the tibia of the patient. The two ends of the traction needle 5 are respectively connected with the two ends of the traction bow 4. The hand wheel 1, the first nut 2, the first screw rod 3, a lifting block locking screw 22, the lifting block 23 and the second guide rail 24 form a pulling mechanism of the traction bow 4. The two second guide rails 24 are fixed at the tail end of the chassis 18. The lifting block 23 can slide up and down along the second guide rail 24 and can be locked by the lifting block locking screw 22. The first nut 2 is rotationally connected with the lifting block 23, in order to adjust the angle of the first screw rod 3, the first screw rod 3 is screwed into the first nut 2, one end of the first screw rod 3 is rotationally connected with a bow back of the traction bow 4, and the other end of the first screw rod is fixed with the hand wheel 1. By rotating the hand wheel 1, the traction bow 4 can be moved, and further the distal end of the tibia of the patient can be pulled by the traction needle 5.

As performing the femoral intramedullary nail implantation operation, it is required to pull the patient's femur, at this time, the second screw rod 13 and the second nut 14 are relatively rotated by rotating the rotating handle 15, and the second screw rod 13 pushes the upper leg back plate 12 to move upwardly (the upper leg back plate 12 slides along the inner hole of the sleeve 16), so that the lower leg of the patient moves upwardly, thereby realizing the traction of the femur.

After a length of the lower limb is restored by traction, if the broken bone is misaligned, the broken bone is restored by the jacking bolt 6, the side pressing bolt 8, the side pressing plate 9, the fixing bolt 10 and the binding band 26. The binding band 26 brings the broken bone close to the lower leg support plate 11 or the upper leg back plate 12, the jacking bolt 6 can keep the broken bone away from the lower leg support plate 11 or the upper leg support 12, and the side pressing bolt 8, the side pressing plate 9 and the fixing bolt 10 apply a lateral thrust force to the broken bone, by integrated use of these components, the misaligned broken bone can be restored.

Tibia Traction Method:

1. placing the device on the operating table and at the lower part of the patient's lower limb 25, adjusting the height of the adjustable legs 17 and the position of the first slide block 21 according to specific conditions of the patient, and thereby resting the upper leg and lower leg of the patient on the upper leg back plate 12 and the lower leg support plate 11;

2. after adjusting the lifting block 23 to a proper height, tightening the lifting block locking screw 22;

3. penetrating the traction needle 5 through the distal ends of the ankle or tibia of the patient, wherein the two ends of the traction needle 5 are connected with the two ends of the traction bow 4, respectively;

4. operating the hand wheel 1 to rotate the first screw rod 3, and the first screw rod 3 pulling the distal end of the tibia to a proper position through the traction bow 4 and the traction needle 5;

5. mounting the jacking bolt 6, the side pressing bolt 8, the side pressing plate 9, the fixing bolt 10, and the binding band 26 at the proper positions of the lower leg support plate 11 to restore the broken bone;

6. performing the intramedullary nail implantation.

The femoral traction method is similar to this, except that the upper leg back plate 12 is jacked up by rotating the second screw rod 13, and the upper leg back plate 12 applies upward force on a knee of the patient, such that the traction of the femur can be realized.

The device can keep the femur or the tibia stably in a restoring state as required for implanting the intramedullary nail without occupying operation space, which is helpful for improving operation quality and operation efficiency, and is suitable for popularization and application in various medical institutions.

Referring to FIGS. 3 to 8, the other embodiment of the lower limb traction device for intramedullary nail implantation operation of the present disclosure differs from the embodiment as shown in FIG. 1 in that:

The lower limb traction device further includes: two third guide rails 28-4 mounted on both sides of the upper leg back plate 12; two sliding frames 28-2 slidably mounted on the two third guide rails 28-4, respectively; and two correcting arms 28-1, one end of which is respectively connected to the top end portions of the two sliding frames 28-2, wherein the correcting arms 28-1 are provided with connecting structures for mounting Kirschner wires 27, and positions of the two correcting arms 28-1 are higher than the lower leg support plate 11.

According to one implementation of the present disclosure, in the lower limb traction device, the correcting arms 28-1 are rotatably connected to the sliding frames 28-2. The lower limb traction device further includes: a fixing arm, one end of which is fixed on the upper portion of the sliding frame 28-2 and positioned under the correcting arm 28-1, and the fixing arm is provided with a threaded hole; and an angle adjusting bolt 28-3 fitted to the threaded hole, one end of the angle adjusting bolt 28-3 abutting against the other end of the correcting arm 28-1 to adjust an angle of the correcting arm 28-1.

According to one implementation of the present disclosure, the lower limb traction device further includes: a sliding frame limiting device, which includes a fixing block 28-5 fixed on the third guide rail 28-4 and provided with a threaded hole; and a limiting bolt 28-6, which is matched with the threaded hole on the fixing block 28-5 and is arranged in parallel with the third guide rail 28-4, and the end portion of the limiting bolt 28-6 is abutted against the bottom end portion of the sliding frame 28-2.

According to one implementation of the present disclosure, the lower limb traction device further includes two Kirschner wires 27 arranged between the connecting structures of the two correcting arms 28-1.

Figure 3:
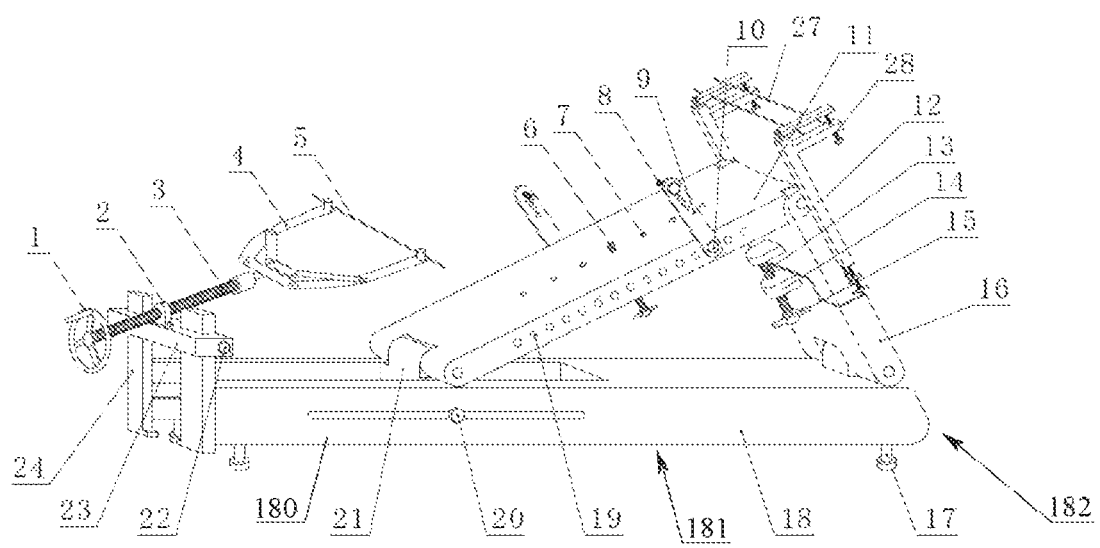
FIG. 3 is a perspective structural schematic view of the other embodiment of the lower limb traction device for intramedullary nail implantation operation of the present disclosure.
Figure 4:
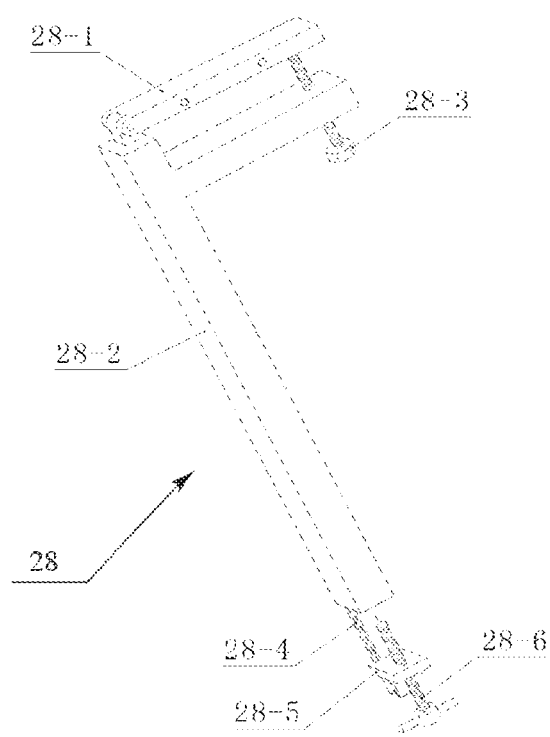
FIG. 4 is a perspective structural schematic view of a sliding frame in the lower limb traction device shown in FIG. 3.
Figure 5:
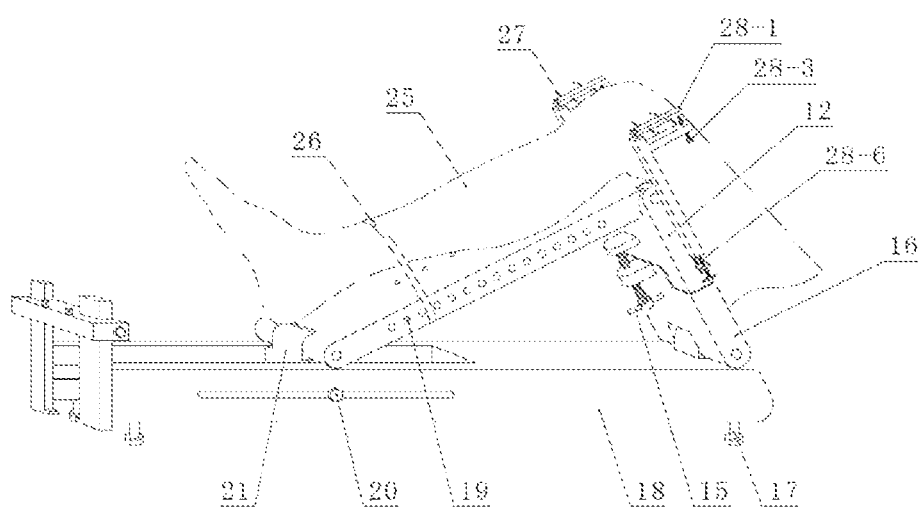
FIG. 5 is a use state schematic view of an intramedullary nail implantation operation for a femur.
Figure 6:
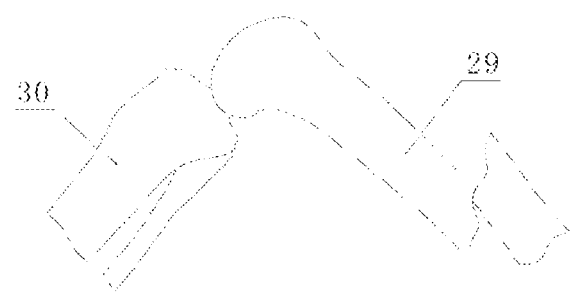
FIG. 6 is a schematic view showing femoral fracture.

In the implementation as shown in FIG. 3, it is possible to perform traction restoration for the femur and the tibia. The lower leg support plate 11, the upper leg back plate 12 and the chassis 18 form a stable triangular support body, for supporting the lower limb 25 of the patient and mounting various traction restoration components (including a femur traction restoration component and a tibia traction restoration component).

The second screw rod 13, the second nut 14, the rotating handle 15 and the sleeve 16 are used for adjusting the height of the upper leg back plate 12, so that the traction on the distal end of the femur can be realized. The two Kirschner wires 27 and the two adjustable brackets 28 are used to adjust an elevation angle and a lateral angle of the distal end of the femur to align and restore the fracture of the femur.

The second guide rail 24, the lifting block 23, the hand wheel 1, the first nut 2, the first screw rod 3, the traction bow 4 and the traction needle 5 are used for pulling the distal end of the patient's tibia. The jacking bolt 6, the side pressing bolt 8, the side pressing plate 9, the fixing bolt 10 and the binding band 26 are used for adjusting the posture of the pulled tibia to restore the broken bone.

As performing the femur intramedullary nail implantation operation, it is required to pull the patient's femur, at this time, the second screw rod 13 and the second nut 14 are relatively rotated by rotating the rotating handle 15, and the second screw rod 13 pushes the upper leg back plate 12 to move upwardly (the upper leg back plate 12 slides along the inner hole of the sleeve 16), so that the lower leg of the patient moves upwardly, and thereby realizing the traction of the femur.

Figure 7:
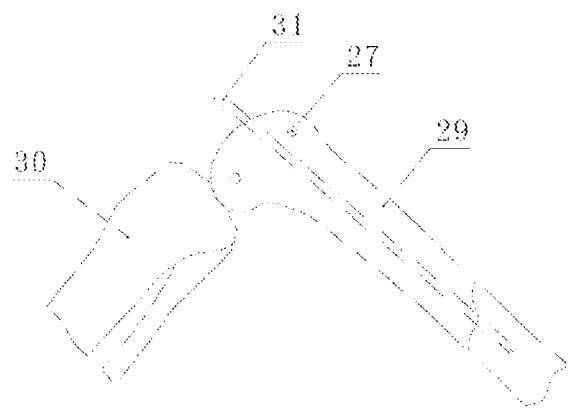
FIG. 7 is a schematic view showing a position of Kirschner wire when a femoral intramedullary nail implantation operation is performed.

After a length of the lower limb is restored by traction, if the fracture of the femur is misaligned, the fracture is aligned by the two Kirschner wires 27 and the two adjustable brackets 28. The two Kirschner wires 27 penetrate through the distal end of femur and are respectively positioned on the both sides of a medullary cavity of the femur (as shown in FIG. 7). The elevation angle of the broken bone can be adjusted by changing the relative heights of the two Kirschner wires 27; the lateral angle of the broken bone can be adjusted by changing the heights of the two ends of the Kirschner wires 27; and the fracture of femur can be aligned and restored by adjusting the lateral angle and the elevation angle of the broken bone. The present disclosure can adjust the relative heights of the two Kirschner wires 27 and the heights of the two ends of the Kirschner wires 27 by using the two adjustable brackets 28, and thereby achieving an aim of aligning the fractures of femur. The relative heights of the two Kirschner wires 27 can be adjusted by the angle adjusting bolt 28-3, and the heights of the two ends of the Kirschner wires 27 can be adjusted by the limiting bolt 28-6.

Femur Traction Restoration Method (See FIGS. 5-7):

1. placing the device on the operating table and at the lower portion of the patient's lower limb 25, adjusting the height of the adjustable legs 17 and the position of the first slide block 21 according to the specific conditions of the patient, and thereby resting the upper leg and lower leg of the patient on the upper leg back plate 12 and the lower leg support plate 11, at this time, it is selective to bind the lower leg on the lower leg support plate 11 with the binding band 26;

2. jacking the upper leg back plate 12 by rotating the second screw rod 13, and the upper leg back plate 12 applies an upward pulling force to the patient's knee to pull the upper leg and restore the length of the patient's upper leg;

3. if the femur fractures cannot be automatically aligned, the two Kirschner wires 27 penetrate through the distal end of the femur of the patient and are respectively positioned on both sides of the medullary cavity of the femur (which does not affect the implantation of intramedullary nails), and the two ends of the Kirschner wires 27 are respectively draped on the correcting arms 28-1 of the two adjustable brackets 28;

4. operating the angle adjusting bolt 28-3 and the limiting bolt 28-6 of the two adjustable brackets 28 to adjust the elevation angle and lateral angle of the distal end of femur to proper positions so as to align the fractures;

5. performing intramedullary nail implantation operation.

Figure 8:
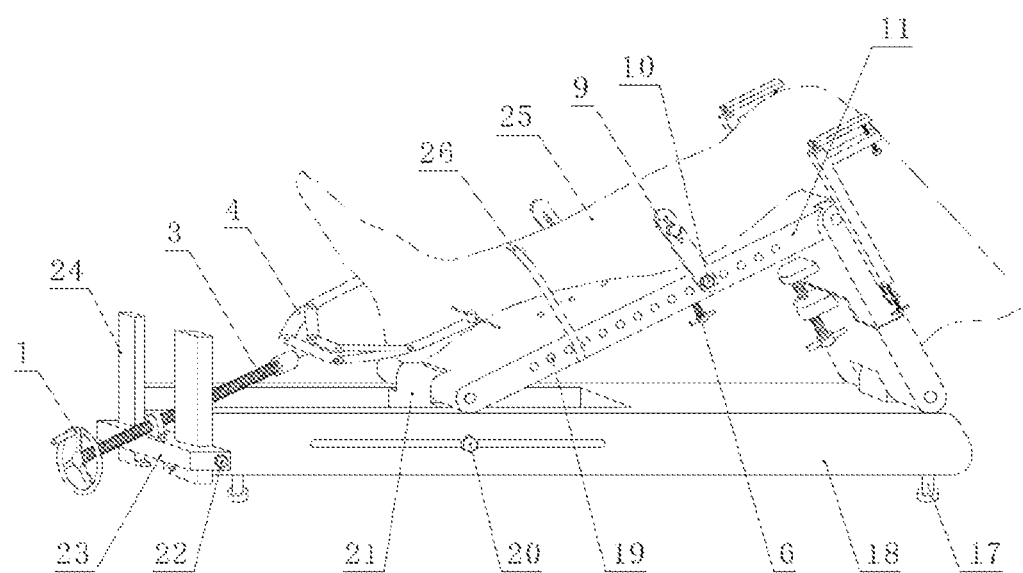
FIG. 8 is a use state schematic view of the intramedullary nail implantation operation for the tibia.

The tibia traction restoration method can also be performed by using the lower limb restoration device for intramedullary nail implantation operation as shown in FIG. 3, referring to FIG. 8:

1. placing the device on the operating table and at the lower part of the patient's lower limb 25, adjusting the height of the adjustable legs 17 and the position of the first slide block 21 according to specific conditions of the patient, and thereby resting the upper leg and lower leg of the patient on the upper leg back plate 12 and the lower leg support plate 11;

2. after adjusting the lifting block 23 to a proper height, tightening the lifting block locking screw 22.

3. penetrating the traction needle 5 through the distal ends of the ankle or tibia of the patient, wherein the two ends of the traction needle 5 are connected with the two ends of the traction bow 4, respectively:

4. operating the hand wheel 1 to rotate the first screw rod 3, and the first screw rod 3 pulling the distal end of the tibia to a proper position through the traction bow 4 and the traction needle 5;

5. mounting the jacking bolt 6, the side pressing bolt 8, the side pressing plate 9, the fixing bolt 10, and the binding band 26 at the proper positions of the lower leg support plate 11 to restore the broken bone;

6. performing the intramedullary nail implantation.

The device can keep the femur or the tibia stably in a restoring state required for implanting intramedullary nails without occupying operation space, which is beneficial to improve operation quality and operation efficiency and is suitable for popularization and application in various medical institutions.

The person skilled in the art, upon consideration of the specification and after practice of this disclosure, would easily conceive of the other embodiments of the present disclosure. The present disclosure is directed to encompass any variation, use or adaptive change, which accord to the general principles of the present disclosure and include common knowledge or the customary means in the art but not disclosed in the present disclosure. The specification and the embodiments are regarded to be illustrative only, and the scope and the spirit of the present disclosure is defined within the claims.

What is claimed is:

1. A lower limb traction device for intramedullary nail implantation operation, comprising:
    a chassis with a first end portion and a second end portion opposite to each other;
    a first slide block slidably provided at a second end portion of the chassis in a longitudinal direction of the chassis;
    a lower leg support plate having two opposite end portions and two opposite side portions, wherein one end portion is connected to the first slide block;
    an upper leg back plate having opposite end portions and opposite side portions, wherein one end portion of the upper leg back plate is connected to the second end portion of the chassis, and the other end portion of the upper leg back plate is connected to the other end of the lower leg support plate;
a pulling mechanism provided at the first end portion of the chassis;
a first guide rail provided at a first end portion of the chassis and extending away from the chassis, wherein the first slide block is provided on the first guide rail;
a second guide rail, fixed to an end portion of the first guide rail away from the chassis, and being perpendicular to the first guide rail; and
a lifting block slidably mounted on the second guide rail, wherein the pulling mechanism is provided on the lifting block.

2. The lower limb traction device according to claim 1, wherein the pulling mechanism comprises:
a first nut mounted on the lifting block;
a first screw rod working in cooperation with the first nut and having an inner end portion facing to the chassis and an outer end portion distanced from the chassis;
a hand wheel mounted on the outer end portion of the first screw rod; and
a traction bow mounted on the inner end portion of the first screw rod, wherein an opening end of the traction bow is provided with a connecting structure capable of mounting a traction needle.

3. The lower limb traction device according to claim 2, further comprising a traction needle provided at the connecting structure of an opening end of the traction bow.

4. The lower limb traction device according to claim 1, further comprising:
a tibia broken bone restoration mechanism, comprising:
at least one jacking assembly provided at a longitudinal central line position of the lower leg support plate; and
at least two side pressing assemblies respectively provided on both sides of the lower leg support plate.

5. The lower limb traction device according to claim 4, wherein the tibia broken bone restoration mechanism further comprises:
a blinding band able to surround the lower leg support plate.

6. The lower limb traction device according to claim 4, wherein a plurality of side mounting holes are provided on both sides of the lower leg support plate in a longitudinal direction, and the side pressing assemblies are selectively mounted in the side mounting holes.

7. The lower limb traction device according to claim 6, wherein the side mounting holes are threaded holes, and the side pressing assembly comprises:
a side pressing plate, with a bottom end portion mounted in the side mounting holes by a fixing bolt, and an upper portion of the side pressing plate provided with a plurality of threaded holes; and
a side pressing bolt selectively fitted to one of the plurality of threaded holes of the side pressing plate and extending to a direction of the lower leg support plate.

8. The lower limb traction device according to claim 4, wherein a plurality of middle mounting holes are provided at a longitudinal central line position of the lower leg support plate, and the jacking assembly is selectively mounted in the middle mounting hole.

9. The lower limb traction device according to claim 8, wherein the middle mounting holes are threaded holes, and the jacking assembly comprises:
a jacking bolt selectively fitted to one of the plurality of the threaded holes.

10. The lower limb traction device according to claim 1, further comprising:
a sleeve having a lower end portion connected to the second end of the chassis, and an upper end portion with an opening;
wherein one end of the upper leg back plate is slidably received in the sleeve with respect to the sleeve.

11. The lower limb traction device according to claim 10, further comprising:
an adjusting mechanism for adjusting a height of the upper leg back plate, comprising:
a second nut fixed on the sleeve;
a second screw rod working in cooperation with the second nut, and having one end connected to the upper leg back plate and the other end equipped with a rotating handle.

12. The lower limb traction device according to claim 1, further comprising:
a femur broken bone restoration mechanism, comprising:
at least one jacking assembly provided at a longitudinal central line position of the upper leg back plate; and
at least two side pressing assemblies respectively provided on both sides of the upper leg back plate.

13. The lower limb traction device according to claim 1, further comprising:
two third guide rails mounted on both sides of the upper leg back plate;
two sliding frames slidably mounted on the two third guide rails, respectively; and
two correcting arms, having end portions respectively connected to top end portions of the two sliding frames, the correcting arms being provided with a connecting structure for mounting Kirschner wires, and positions of the two correcting arms being higher than the lower leg support plate.

14. The lower limb traction device according to claim 13, wherein the correcting arm is rotatably connected to the sliding frame, and the lower limb traction device further comprises:
a fixing arm, having one end fixed on an upper portion of the sliding frame and positioned under the correcting arm, and the fixing arm being provided with a threaded hole; and
an angle adjusting bolt fitted to the threaded hole, one end of the angle adjusting bolt abuts against the other end of the correcting arm to adjust an angle of the correcting arm.

15. The lower limb traction device according to claim 13, further comprising:
a sliding frame limiting device, comprising:
a fixing block, fixed to the third guide rail and provided with a threaded hole; and
a limiting bolt matched with the threaded hole on the fixing block and provided in parallel with the third guide rail, and an end portion of the limiting bolt abuts against the bottom end portion of the sliding frame.

16. The lower limb traction device according to claim 13, further comprising two Kirschner wires provided between the connecting structures of the two correcting arms.

17. The lower limb traction device according to claim 1, wherein an upper surface of the lower leg support plate or the upper leg back plate has an arc-shaped concave surface.

18. The lower limb traction device according to claim 1, wherein adjustable legs are provided on the bottom portion of the chassis.

* * * * *